United States Patent
Jarding et al.

(10) Patent No.: US 6,275,735 B1
(45) Date of Patent: Aug. 14, 2001

(54) METHODS AND APPARATUS FOR ELECTRICAL MICROCURRENT STIMULATION THERAPY

(75) Inventors: John B. Jarding, Hot Springs, SD (US); George D. O'Clock, North Mankato, MN (US)

(73) Assignee: BionErgy Therapeutics, Inc., Hot Springs, SD (US)

( * ) Notice: Subject to any disclaimer, the term of this patent is extended or adjusted under 35 U.S.C. 154(b) by 0 days.

(21) Appl. No.: 09/346,772

(22) Filed: Jul. 7, 1999

Related U.S. Application Data

(63) Continuation-in-part of application No. 09/114,815, filed on Jul. 13, 1998, now Pat. No. 6,035,236.

(51) Int. Cl.$^7$ .............................. A61N 1/32; A61N 1/36
(52) U.S. Cl. ................... 607/53; 607/66; 607/68
(58) Field of Search ................... 607/53, 66–69, 607/54

(56) References Cited

U.S. PATENT DOCUMENTS

| | | |
|---|---|---|
| 4,541,432 | 9/1985 | Molina-Negro et al. . |
| 4,989,605 | 2/1991 | Rossen . |
| 5,395,398 | 3/1995 | Rogozinski ............................ 607/50 |
| 5,397,338 * | 3/1995 | Grey et al. ............................ 607/115 |
| 5,522,864 | 6/1996 | Wallace et al. . |
| 5,573,552 | 11/1996 | Hansjurgens . |
| 5,578,060 | 11/1996 | Pohl et al. . |
| 5,800,477 | 9/1998 | Groux ...................................... 607/76 |
| 5,935,156 * | 8/1999 | Chandler et al. ........................ 607/66 |
| 6,115,637 * | 9/2000 | Lennox et al. .......................... 607/68 |

OTHER PUBLICATIONS

Ngok Cheng, M.D. et al., "The Effects of Electric Currents on ATP Generation, Protein Synthesis, and Membrane Transport in Rat Skin," *Clinical Orthopaedics and Related Research*, No. 171, Nov.–Dec. 1982, pp. 264–271.

Joel Rossen, DVM, Ph.D., "Flipping the Switch, Managing Pain with Microcurrent Stimulation," *Physical Therapy Today*, Electrotherapy Issue, vol. 3, No. 13, Mar. 27, 1995, pp. 4–7.

Leland D. Michael, O.D., "Nutritional Supplementation, Electrical Stimulation and Age Related Macular Degeneration," *Journal of Orthomolecular Medicine*, Third Quarter 1993, vol. 8, No. 3, pp. 168–171.

David A. Newsome, M.D., "Oral Zinc in Macular Degeneration," *Arch Ophthalmol*, vol. 106, Feb. 1988, pp. 192–199.

"Tensmac=Ekectro–Stimulation of The Retina," *The Geriatrician*, vol. 4, Issue 5, 1997, pp. 5–6.

* cited by examiner

*Primary Examiner*—Carl H. Layno
(74) *Attorney, Agent, or Firm*—Townsend and Townsend and Crew LLP

(57) ABSTRACT

A method and apparatus for providing microcurrent stimulation therapy to a body part is disclosed. In one embodiment, a method allows digital control of the modulation frequency of the microcurrent signal. The method includes receiving a first digital data word which is used to produce a first frequency related to the first digital data word, whereupon, a first microcurrent signal at the first frequency is applied to the body part. A second digital data word is received and used to produce a second frequency related to the second digital data word. A second microcurrent signal at the second frequency is applied to the body part. In another embodiment, a method allows direct digital synthesis of the microcurrent stimulation signal. A first digital data word is used to produce a first analog voltage which is applied to the body part. A second digital data word is used to produce a second analog voltage which is also applied to the body part, where the first analog voltage is different from the second analog voltage. In yet another embodiment, an apparatus for providing microcurrent stimulation therapy includes a digital-to-analog converter, a controller and a plurality of data words. The controller is coupled to the digital-to-analog converter and supplies the digital-to-analog converter with digital data words in order to generate an electrical signal for the microcurrent stimulation therapy.

23 Claims, 9 Drawing Sheets

METHODS AND APPARATUS FOR ELECTRICAL MICROCURRENT STIMULATION THERAPY

CROSS-REFERENCES TO RELATED APPLICATIONS

This application is a continuation-in-part of and claims the benefit of U.S. patent application Ser. No. 09/114,815, filed Jul. 13, 1998, now U.S. Pat. No. 6,035,236, the disclosure of which is incorporated by reference.

BACKGROUND OF THE INVENTION

The present invention relates generally to methods and apparatus for electrical microcurrent stimulation therapy, and more particularly to methods and apparatus for providing electrical microcurrent stimulation around an eye to combat visual system diseases, such as macular degeneration.

Chronic pain is a problem for millions of individuals throughout the world. One method of treating such pain is to provide microcurrent stimulation around or near the areas where the pain is occurring. Microcurrent, which typically is defined as current below 1 milliamp, can provide rapid and long-lasting pain relief for a wide variety of pain syndromes. Generally, microcurrent stimulation therapy typically comprises applying a current in the range of about 20 to about 300 microamps to the affected area. The current or microcurrent blocks neuronal transmission of pain signals and stimulates the release of endorphins to help relieve the pain in chronic and acute pain patients.

While the current level can be an important factor in microcurrent stimulation therapy, frequency modulation and the waveform of the electrical signal are also important. Some electrical stimulation therapy devices currently known in the art typically allow the user to manually adjust the frequency ranges and types of waveform signals applied to the patient. For example, the MicroStim 400 device, manufactured by MicroStim, Inc., located in Tamarac, Fla., features a combination of a carrier waveform having a modulated frequency thereon. The MicroStim device is covered by U.S. Pat. No. 4,989,605, issued on Feb. 5, 1991 to Joel Rossen and entitled "Transcutaueous Electrical Nerve Stimulation (TENS) Device", the contents of which is incorporated herein by reference. The theory behind the MicroStim 400 device is that the carrier wave is designed to take the modulated frequency deep into the body for consistent and rapid pain relief. However, a disadvantage of the MicroStim 400 device is that the signal that it generates produces most of its power at individual frequencies 105. That is, when viewing the signal produced by the MicroStim 400 in the frequency domain, the majority of the power output from the signal resides at discrete frequencies. Accordingly, the therapeutic effect of the signal may not be maximized.

Another device which can be used for microcurrent stimulation therapy is the Amrex Z-Stim device manufactured by Amrex, Corp. of Carson, Calif. The Z-Stim device is a multi-signal interferential stimulator that provides multiple swept frequency sinusoidal signals. The applications for sinusoidal signals are more appropriate for muscle stimulation and addressing problems associated with pain, edema and rehabilitation for certain neuromuscular and orthopedic problems.

In addition to chronic pain relief, microcurrent therapy is being used to treat a number of visual system diseases, including macular degeneration and retinitis pigmentosa.

Age-related macular degeneration (AMD) is the leading cause of legal blindness in the United States in persons over 65 years old. According to a March 1997 Review of Optometry Journal, 10% of our population over age 52 has AMD and 33% of individuals over age 75 have AMD. It is estimated that more than 13 million Americans now have AMD and that, by the time the Baby Boomers reach age 65, there will be over 30 million cases of AMD, almost 25% of our population over 65.

Normal retinal cell function is a photochemical reaction converting light energy to an electrical impulse which travels to the brain and vision occurs. With AMD and other visual system diseases, diseased, inflamed retinal cells eventually lose cell function. Adenosine triphosphate (ATP) levels drop, protein synthesis drops, the electrical resistance goes up, and cell membrane electrical potential goes down. Basically, the cells seem to go dormant for a time before they die. It is believed that, if electrical stimulation is provided to the cells before they die, blood vessel permeability is increased, a more normal cellular electrical potential will be achieved, the ATP levels will increase, protein synthesis will occur again, and normal cell metabolism will be restored. In addition, electrical stimulation appears to have a healing effect on the small blood vessels in the retina, promoting a more efficient delivery of nutrients to the retinal cells and a more efficient uptake of proteins that can accumulate on the retina. Thus, it is believed that microcurrent stimulation will help rejuvenate the cells in the retina to slow or stop degeneration of the eye due to AMD. With the proper microcurrent stimulation waveform and therapy procedures, AMD may be slowed or stopped in a large number of people suffering from the disease.

While microcurrent stimulation therapy has been used to treat AMD and other visual system diseases, the methods and apparatus used in the prior art do not appear to maximize the therapeutic effect. For example, as mentioned briefly above, the devices for providing microcurrent stimulation therapy are limited in the types of waveforms and frequency ranges which they may provide for therapy.

SUMMARY OF THE INVENTION

Accordingly, it is an advantage of the present invention to provide novel methods and apparatus for providing microcurrent stimulation therapy to a body part to combat chronic pain, injury, or disease in that body part.

Another advantage of the present invention is to provide methods and apparatus for treating various diseases, including macular degeneration and retinitis pigmentosa.

Yet another advantage of the present invention is to provide an apparatus which generates unique waveforms that can be used for microcurrent stimulation therapy. The unique waveforms produce a spectral response desired for treating the disease of interest.

Still another advantage of the present invention is to provide an apparatus which can produces unique waveforms under digital control by using either digitally controlled frequency modulation or direct digital synthesis. Digital control can provide more precision and versatility in the control of the spectral output for microcurrent therapy.

The above and other advantages of the present invention are carried out in one embodiment by an apparatus for supplying an electrical signal to a body part in order to provide microcurrent stimulation therapy to the body part. In this embodiment, the apparatus includes a digital-to-analog converter, a controller and a plurality of data words. The controller is coupled to the digital-to-analog converter and supplies the digital-to-analog converter with digital data words in order to generate an electrical signal to a voltage controlled oscillator which serves as the basic source for the microcurrent stimulation therapy.

In another embodiment, a method allows digital control of the modulation frequency of the microcurrent signal preferably using a look-up table. The method includes receiving a first digital data word which is used to produce a first frequency related to the first digital data word, whereupon, a first microcurrent signal at the first frequency is applied to the body part. A second digital data word is received and used to produce a second frequency related to the second digital data word. A second microcurrent signal at the second frequency is applied to the body part.

In yet another embodiment, a method allows direct digital synthesis of the microcurrent stimulation signal. A first digital data word is used to produce a first analog voltage which is applied to the body part. A second digital data word is used to produce a second analog voltage which is also applied to the body part, where the first analog voltage is different from the second analog voltage.

BRIEF DESCRIPTION OF THE DRAWINGS

A more complete understanding of the present invention may be derived by referring to the detailed description and claims when considered in connection with the figures, wherein like reference numbers refer to similar items throughout the figures, and:

FIG. 5b illustrates the spectral or frequency response of the sinusoidal wave signal of FIG. 5a;

FIG. 6b illustrates the spectral or frequency response of the square wave signal of FIG. 6a;

FIG. 7b is the spectral or frequency response of the waveform signal of FIG. 7a;

FIG. 8b is the spectral or frequency response of the waveform signal of FIG. 8a;

DESCRIPTION OF THE SPECIFIC EMBODIMENTS

The present invention comprises methods and apparatus for providing microcurrent simulation therapy for the treatment of chronic pain, visual system diseases and other bodily defects or diseases. More particularly, the present invention relates to a microcurrent waveform generator which generates sweep wave signals for use in microcurrent stimulation therapy. As discussed in more detail below, the microcurrent sweep wave generator disclosed herein may be used for any type of microcurrent stimulation therapy and will find its greatest use in treating patients suffering from macular degeneration.

In addition, the present invention relates to a novel method for treating visual system diseases such as macular degeneration and retinitis pigmentosa using microcurrent stimulation therapy techniques.

Figure 1:
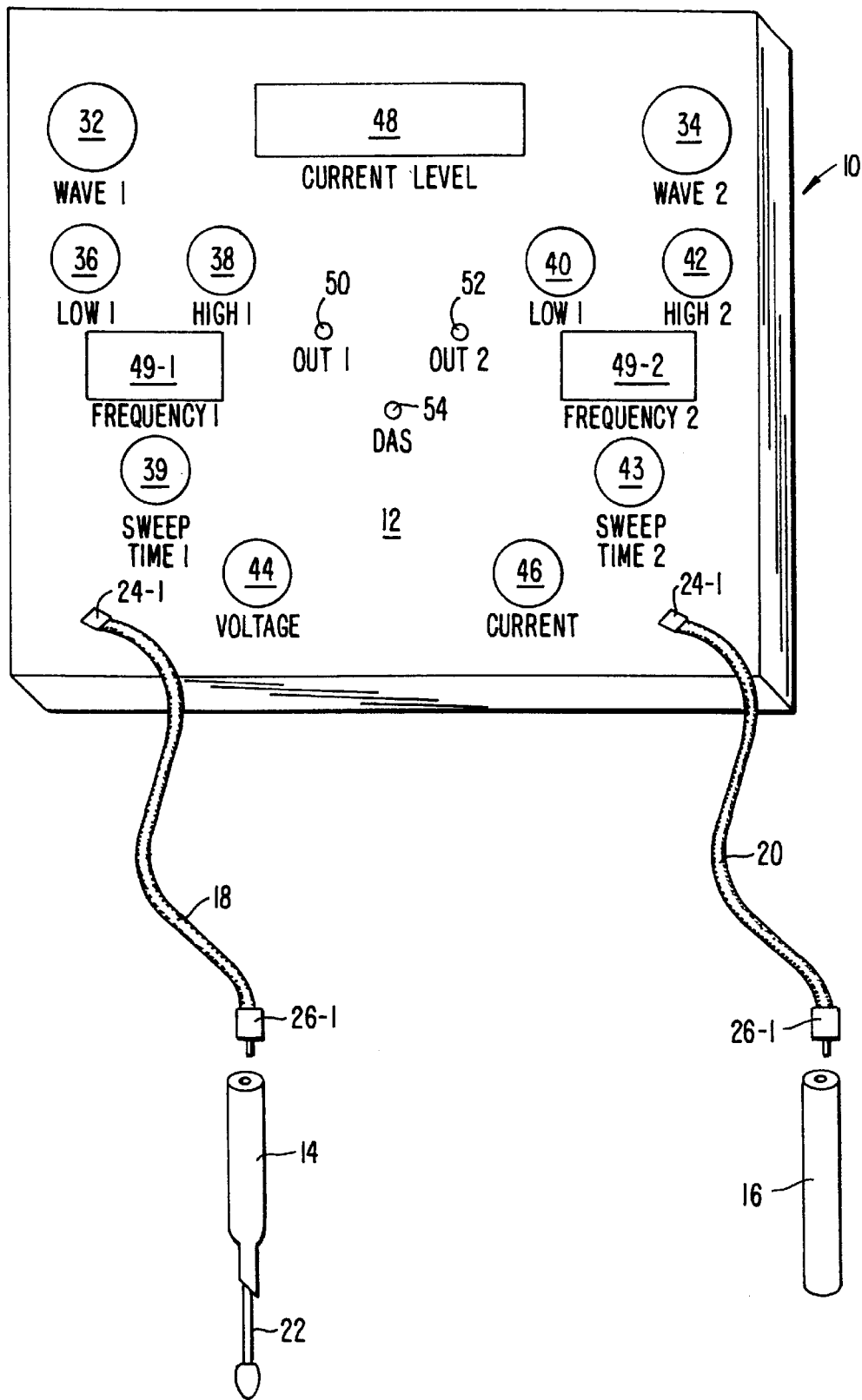
FIG. 1 is a diagram of a microcurrent stimulation therapy apparatus having a microcurrent signal generator and a probe for applying the microcurrent to a body part.

With reference to FIG. 1, a novel microcurrent stimulation therapy apparatus 10 is shown in accordance with the present invention. Therapy apparatus 10 preferably comprises a sweep wave signal generator 12, a stimulation probe 14, and an electrode 16. Preferably, stimulation probe 14 is connected to sweep wave signal generator 12 via a first electrical connector 18, and electrode 16 is connected to sweep wave signal generator 12 via a second electrical connector 20. As illustrated in FIG. 1, a probe tip 22 preferably is connected to the end of stimulation probe 14 opposite the end of probe 14 connected to first electrical connector 18.

Stimulation probe 14 preferably comprises a shielded hand-held probe configured to administer microcurrent stimulation to various points on one or more body parts. In accordance with a preferred embodiment of the present invention, probe tip 22 preferably comprises a cotton swab moistened or dampened with a conductive gel. The dampened cotton swab allows for the gentle administration of the microcurrent to the body part without undue discomfort. However, while one embodiment of the present invention illustrates a probe tip 22 as being a cotton swab, one skilled in the art will appreciate that other types of probe tips may be used. For example, probe tip 22 may be made from a variety of different metals like copper, brass, aluminum, or the like, or probe tip 22 may be made from metal combinations or other conductive materials. In any event, any suitable probe tip may be used and, thus, the present invention is not limited to the illustrated embodiment.

In accordance with a preferred embodiment of the present invention, electrode 16 preferably comprises a handheld brass electrode. As one skilled in the art will appreciate, when a patient receiving microcurrent stimulation therapy holds electrode 16, a closed circuit is created with stimulation probe 18. That is, by holding electrode 16, current from probe 18 will travel through the body, to brass electrode 16 and back to sweep wave signal generator 12.

While the illustrated embodiment shows a handheld brass electrode 16, any electrode configuration may be used. For example, electrode 16 may be a conductive clip device which attaches to a body part such as a finger, ear, arm or the like.

As discussed briefly above, first electrical connector 18 is configured to connect stimulation probe 14 to sweep wave signal generator 12, and second electrical connector 20 is configured to connect electrode 16 to sweep wave signal generator 12. In the illustrated embodiment, first and second electrical connectors 18 and 20 each preferably include a first connector end 24 for connection to generator 12 and a second connector end 26 for connection to stimulation probe 14 and electrode 16, respectively. In accordance with this aspect of the invention, connectors 18 and 20 are removable from generator 12 and probe 14 and electrode 16.

In accordance with an alternative embodiment of the present invention, connectors 18 and 20 may be hardwired to generator 12, or to probe 14 and electrode 16, or to both generator 12 and probe 14 and electrode 16. In addition, in accordance with yet another alternative embodiment of the present invention, electrical connectors 18 and 20 may comprise any suitable electrical connection device currently known in the art or hereinafter developed.

Still referring to FIG. 1, a more detailed description of sweep wave signal generator 12 will now be discussed. As discussed in detail below, sweep wave signal generator 12 preferably is configured to generate one or more sweep wave signals having various waveform, sweep frequency, sweep time, duty cycle, center frequency, frequency window, and amplitude characteristics. In accordance with a preferred embodiment of the invention, the generated sweep wave signal(s) are frequency varied signals. That is, the frequency of the signals vary over time.

To generate the different sweep wave signals, sweep wave signal generator 12 may produce a single sweep wave signal, or alternatively, sweep wave signal generator 12 may generate a composite signal comprising two independent swept wave signals or a swept wave signal and a non-swept wave signal. In accordance with this aspect of the present invention, sweep wave signal generator 12 preferably comprises a first waveform control 32 and a second waveform control 34. First waveform control 32 preferably controls the waveform type of a first sweep wave signal, and second waveform control 34 preferably controls the waveform type of a second sweep wave signal. First and second waveform controls 32 and 34 may be adjusted to produce a variety of different sweep waveforms. For example, by adjusting first and second controls 32 and 34, generator 12 will produce different waveforms, including sinusoidal waveforms, ramp waveforms, triangular waveforms, rectangular or square waveforms, step waveforms, window waveforms, unipolar waveforms, bipolar or bi-phasic waveforms or steady-state DC signals, to name a few. By combining different waveform types having different sweep frequencies and sweep times, a large variety of therapeutic sweep waves may be generated.

In addition to controlling the type of waveforms generated, sweep wave signal generator 12 preferably is configured to control the range of frequencies between which the selected waveforms sweep, as well as the sweep time for performing the sweep of frequency ranges. In accordance with this aspect of the invention, generator 12 preferably has a first low frequency control 36, a first high frequency control 38, a first sweep time control 39, a second low frequency control 40, a second high frequency control 42, and a second sweep time control 43. First low frequency control 36 preferably controls the low frequency threshold for the first sweep wave signal, first high frequency control 38 controls the high frequency threshold of the first sweep wave signal, and first sweep time control 39 controls the sweep time of the first sweep wave signal. Similarly, second low frequency control 40 preferably controls the low frequency threshold of the second sweep wave signal, second high frequency control 42 controls the high frequency threshold of the second sweep wave signal, and second sweep time control 43 controls the sweep time of the second sweep wave signal.

In accordance with a preferred embodiment of the present invention, the low frequency thresholds for both sweep wave signals may be in the range of about 0 Hz to about 400 Hz. Similarly, the high frequency threshold for the two sweep wave signals may be in the range of about 0 Hz to about 2000 Hz. The sweep time for both the first and the second sweep wave signals preferably is in the range of about 7 seconds to about 60 seconds, and more preferably about 15 seconds. While the illustrated embodiment shows a low frequency control and a high frequency control for each sweep wave signal, one skilled in the art will appreciate that any frequency control scheme may be used. For example, each sweep wave signal may have only one frequency control, or one low and one high frequency control may control both sweep wave signals. In any event, the present invention is not limited to the illustrated embodiment.

Still referring to FIG. 1, sweep wave signal generator 12 preferably further comprises a voltage signal control 44, a current control 46, a first signal monitor port 50, a second signal monitor port 52, and a data-acquisition system port 54.

As discussed in more detail below with reference to FIGS. 2 and 3, sweep wave signal generator 12 preferably further comprises a voltage limiting circuit and a current limiting circuit. In accordance with this aspect of the invention, voltage control 44 is configured to control the magnitude of the voltage signal peak or peak-to-peak output. Similarly, current control 46 preferably is configured to control the current supplied to the body part of the patient by controlling the current limiting circuit.

As discussed in greater detail below, sweep wave signal generator 12 may be connected to one or more oscilloscopes, spectrum analyzers or waveform displays via first and second signal monitor ports 50 and 52. By connecting generator 12 to one or more oscilloscopes, spectrum analyzers, or waveform displays, the waveform signal and current level at various locations within the generator circuit can be monitored. In addition, sweep wave signal generator 12 may further include a data-acquisition port 54 for connecting generator 12 to a data-acquisition system and/or a strip chart recorder. In accordance with this aspect of the present invention, generator 12 preferably is configured to record various data, such as waveform, current and voltage levels, and the like for different patients, and then download the data to a data-acquisition system for monitoring and analysis. In this manner, a doctor or practitioner can analyze data concerning variations in current levels between patients and different diseases of the visual system, as well as variations in the swept waveform for different patients and disease states. The doctor or practitioner can then use this data to track therapy progress, develop better therapy procedures for different patients, and monitor variabilities in treatment points. In addition, the doctor or practitioner can monitor probe contact consistency and patient progress for self-administered therapy patients. That is, for patients who use or administer the micro-current stimulation therapy to themselves, at home, the doctor or practitioner can use the collected data to determine whether the patient is administering the therapy correctly and whether the therapy protocol needs to be adjusted for that particular patient.

As one skilled in the art will appreciate, sweep wave signal generator 12 may include both voltage control 44 and current control 46, or generator 12 may be configured with only one of the two controls. For example, by controlling the magnitude of the voltage output signal for a given patient impedance, the current supplied to the patient is also controlled. Similarly, by controlling the current supplied to a patient having a given impedance, the voltage is also controlled. Thus, the present invention is not limited to the illustrated embodiment. In addition, while the illustrated embodiment of sweep wave signal generator 12 shows a number of different control features, one skilled in the art will appreciate that certain control features may be eliminated and other control features may be added without departing from the spirit of the invention. For example, while not illustrated in the figures, sweep wave signal generator 12 may further comprise duty cycle controls for controlling the duty cycles of the first and second sweep wave signals.

Finally, sweep wave signal generator 12 preferably further comprises a current level indicator 48, a first frequency indicator 49-1, and a second frequency indicator 49-2. In accordance with this aspect of the invention, current level indicator 48 preferably displays the current being supplied to the patient. Current level indicator 48 may be configured to display root-mean-square (rms) or average current output for certain segments of treatment time.

In addition, in accordance with one embodiment of the present invention, first and second frequency indicators 49-1 and 49-2 preferably are configured to display the frequency of the first and second sweep wave signals, respectively, as the signal sweeps through the frequency ranges. Alternatively, in accordance with another embodiment of the present invention, first and second frequency indicators 49-1 and 49-2 may be configured to display the frequency ranges between which the first and second sweep waves are to sweep.

Figure 2:
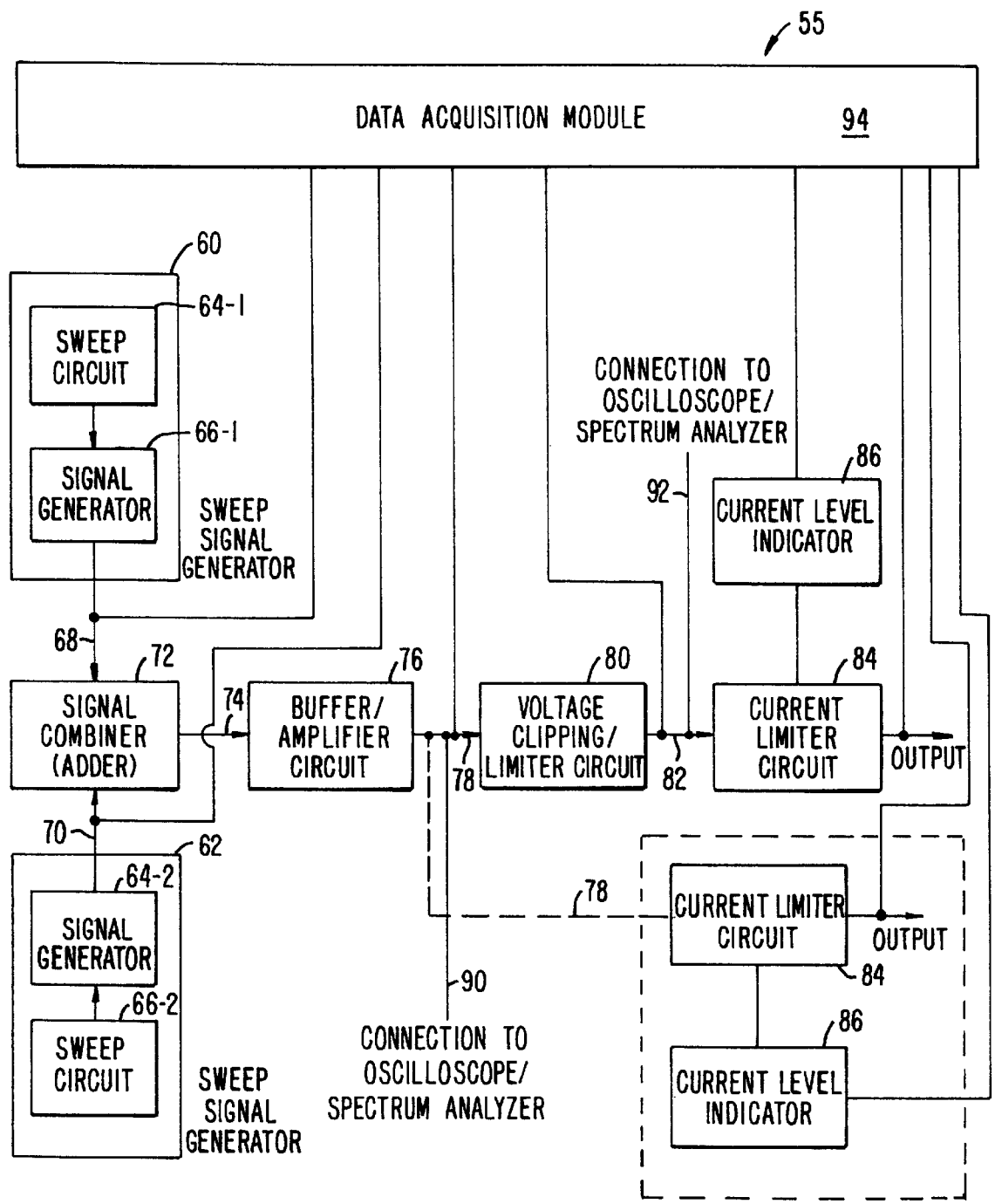
FIG. 2 is a block diagram of a circuit embodying the microcurrent signal generator of FIG. 1.

Referring now to FIG. 2, a block circuit diagram of one embodiment of a sweep wave signal generator circuit 55 is illustrated. In accordance with a preferred embodiment of the present invention, sweep wave signal generator circuit 55 preferably comprises a first sweep signal generator 60, and a second sweep signal generator 62. Both first and second sweep wave signal generators 60, 62 preferably comprise a sweep control circuit 64 and a signal generator 66. Sweep control circuit 64 preferably controls the sweep frequencies, sweep times and duty cycles of the signals, and signal generator 66 preferably generates a particular waveform having the sweep frequencies, sweep times and duty cycles dictated by control circuit 64. First and second sweep wave signal generators 60 and 62 may be configured to generate swept waves, or non-swept waves. For example, by setting the high and low sweep frequencies to the same frequency for a particular signal, the signal generator will generate a signal having a set frequency.

As one skilled in the art will appreciate, first and second sweep signal generators 60 and 62 may comprise any suitable sweep signal generator currently known in the art. For example, function generator with sweep control, product no. PM5132, manufactured by Philips Corporation, may be used. As discussed briefly above, sweep signal generator 60 and 62 may be configured to generate a wide variety of waveforms having a variable range of sweep frequencies and sweep times.

In accordance with the embodiment illustrated in FIG. 2, first sweep signal generator 60 preferably generates a first sweep wave signal 68 and second sweep signal generator 62 preferably generates a second sweep wave signal 70. A signal combiner/adder circuit 72 preferably receives first sweep wave signal 68 and second sweep wave signal 70 and combines the two signals into a single sweep wave signal 74. From combiner/adder circuit 72, sweep wave signal 74 preferable passes to a buffer/amplifier circuit 76, which is configured to amplify and buffer single sweep wave 74, generating a buffered sweep wave signal 78.

In accordance with one embodiment of the present invention, buffered sweep wave signal 78 preferably passes into a voltage clipping or limiting circuit 80, which is configured to control the polarity of the output voltage to a predetermined voltage level and polarity. The output of clipping or limiting circuit 80 is a clipped voltage signal 82 which preferably passes to a current limiting circuit 84 configured to limit the total current output supplied to a particular body part. Connected to current limiting, circuit 84 is a current level indicator 86, which preferably is a volt meter configured to monitor and display the output current level.

As mentioned briefly above, sweep wave signal generator 12 preferably comprises a voltage control 44 and a current control 46. In accordance with this aspect of the invention, voltage control 44 preferably is configured to control the voltage signal peak or peak-to-peak output from voltage clipping or limiting circuit 80. For example, by adjusting voltage signal control 44, voltage clipping or limiting circuit 80 is adjusted so that the amplitude of the output voltage changes as necessary. Similarly, current control 46 of signal generator 12 preferably is configured to control the current output from current limiting circuit 84.

Current level indicator 86 may comprise any suitable current measuring and displaying device. As discussed in more detail below with reference to FIG. 3, current level indicator 86 may comprise, for example, a voltage measuring device configured across current limiting circuit 84. As one skilled in the art will appreciate, the amount of current flowing through current limiting circuit 84 is a function of the voltage across the circuit, as well as the resistance of the circuit itself. Once the current level is determined, current level indicator 86 preferably displays the current level on current level display 48 of signal generator 12 (see FIG. 1). Current level indicator 86 can be configured to measure the root-mean-square (RMS) current, or indicator 86 may be configured to measure an average current over a particular time period.

In accordance with another preferred embodiment of the present invention, signal generator circuit 55 may be configured without voltage clipping or limiting circuit 80. In accordance with this preferred embodiment of the invention, amplified sweep wave signal 78 passes directly to current limiting circuit 84. This particular embodiment of the invention is illustrated in FIG. 2 as dotted line 78 passing into circuit 88 comprising current limiting circuit 84 and current level indicator 86. In accordance with this second embodiment of the present invention, current limiting circuit 84 and current level indicator 86 preferably operate in the same general manner as that described above with reference to the first embodiment. Accordingly, a detailed discussion of circuit 88 will not be discussed further.

In accordance with yet another embodiment of the present invention, sweep wave signal generating circuit 55 may further comprise connections 90 and 92 for connection to one or more oscilloscopes, spectrum analyzers or waveform displays. As illustrated in FIG. 2, in accordance with a preferred embodiment of the present invention, signal generating circuit 55 preferably has two connections, one prior to voltage clipping or limiting circuit 80 and one after voltage clipping or limiting circuit 80. In accordance with this aspect of the invention, an oscilloscope, spectrum analyzer, or waveform display connected to connection 90 will display the waveform of the sweep wave signal from buffer/amplifier circuit 76, and the second oscilloscope, spectrum analyzer, or waveform display connected to connection 92 will display the sweep wave signal after it has passed through voltage clipping or limiting circuit 80. Accordingly, the operator of the device can be sure that voltage clipping or limiting circuit is functioning properly by analyzing the signals entering and leaving the circuit. In the embodiment in which the voltage clipping or limiting circuit is eliminated, only one connection to an oscilloscope or spectrum analyzer is present.

In addition, as mentioned briefly above, the sweep wave signal generator circuit 55 may further comprise a data acquisition module 94 for collecting data about the performance of the therapy device, and in particular, generator circuit 55. For example, in accordance with the illustrated embodiment, data acquisition module 94 preferably is connected so that it can monitor first and second sweep waves 68 and 70, buffered sweep wave signal 78, clipped voltage signal 82, and the current and voltage of the output signals. In accordance with this aspect of the invention, the collected data can then be downloaded to data acquisition system for analysis by a doctor or therapist. As one skilled in the art will appreciate, the data acquisition system may comprise any suitable data acquisition system, such as a computer system configured to manipulate and display such data.

Figure 3:
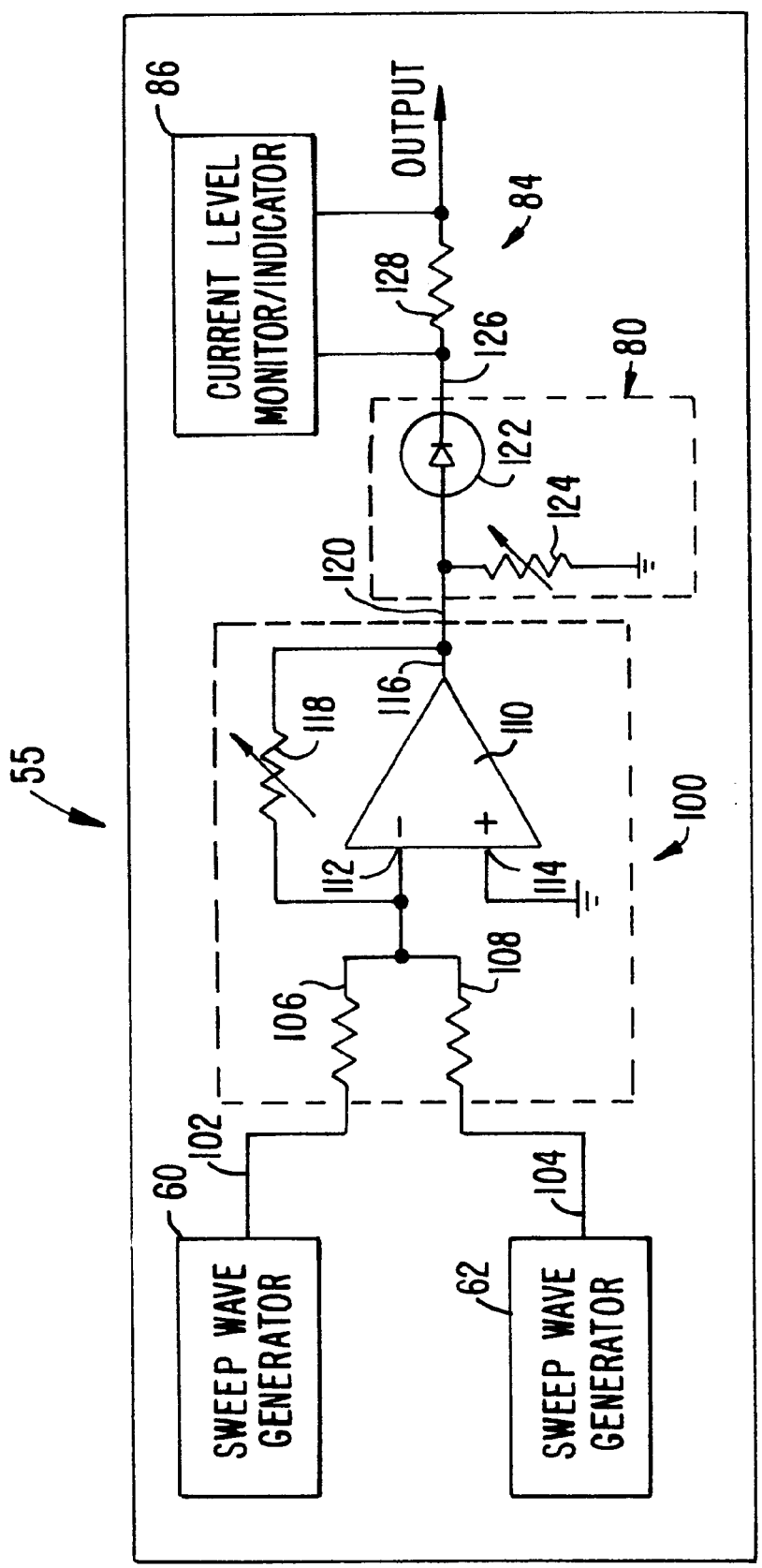
FIG. 3 is a detailed circuit diagram of one embodiment of the microcurrent signal generator circuit of FIG. 2.

Referring now to FIG. 3, a detailed circuit diagram of one embodiment of sweep wave signal generating circuit 55 is illustrated. In accordance with the illustrated embodiment in FIG. 3, signal generating circuit 55 preferably comprises a first sweep wave signal generator 60, a second sweep wave signal generator 62, a signal combiner or adder circuit 72 a buffer/amplifier circuit 76, a voltage limiting or clipping circuit 80, a current limiting circuit 84 and a current level monitor/indicator 86.

In accordance with this particular embodiment of the present invention, signal adder or combiner circuit 72 and buffer/amplifier circuit 76 preferably are combined into a single operational amplifier circuit 100. Op amp circuit 100 preferably receives a first sweep wave signal 102 from first sweep wave signal generator 60 and a second sweep wave signal 104 from second sweep wave signal generator 62. In accordance with this aspect of the invention, first sweep wave signal 102 is connected to negative input terminal 112 of an op amp 110 through a first resistor 106, and second sweep wave signal 104 is connected to negative input terminal 112 of op amp 110 through a second resistor 108. First resistor 106 and second resistor 108 preferably are in the range of about 1 kiloohm to about 25 kiloohms, and more preferably are about 10 kiloohms.

Op amp 110 further comprises a positive input terminal 114 which preferably is connected to ground, and an output terminal 116 which preferably is connected in a negative feedback loop to negative input terminal 112 through a variable resistor 118. In accordance with a preferred embodiment of the present invention, variable resistor 118 may have a variable resistance which ranges between about 1 to about 50 kiloohms, and more preferably ranges between about 3.3 to about 7.8 kiloohms.

While one embodiment of the present invention disclosed herein utilizes an op amp as a signal adder and buffer amplifier, one skilled in the art will appreciate that other circuit configurations may be used to accomplish the amplifier, adder, and buffering tasks. Thus, the present invention is not limited to an embodiment comprising an op amp circuit.

From operational amplifier circuit 100, a single sweep wave signal 120 passes into voltage clipping or limiting circuit 80. In accordance with this aspect of the invention, voltage clipping or limiting circuit 80 preferably comprises a diode 22 and a variable resistor 124. Variable resistor 124 is connected between a first terminal of diode 122 and ground. With this particular configuration, the adjustment of variable resistor 124 preferably adjusts the limit of the voltage amplitude output. In accordance with a preferred embodiment of the invention, variable resistor 124 preferably has a resistance which ranges between about 5 to about 50 kiloohms, and more preferably between about 15 to about 25 kiloohms.

While the illustrated embodiment of the present invention shows voltage clipping or limiting circuit 80 comprising a resistor/diode combination, one skilled in the art will appreciate that any voltage limiting circuit configuration may be used. For example, instead of a diode/resistor combination, voltage clipping or limiting circuit 80 may comprise an operational amplifier configured as a limiting circuit. Therefore, the present invention is not limited to the illustrated embodiment.

From voltage limiting circuit 80, a clipped wave signal 126 preferably passes into current limiting circuit 84. In accordance with the illustrated embodiment of the invention, current limiting circuit 84 comprises a resistor 128. As one skilled in the art will appreciate, since current equals the voltage divided by the resistance (I=V/R), the higher the value of the resistor 128, the lower the current output. In accordance with the preferred embodiment of the invention, resistor 128 preferably has a value between about 10 and about 500 kiloohms, and more preferably a value between about 20 kiloohms and about 115 kiloohms.

While the illustrated embodiment shows resistor 128 as a constant resistance value, one skilled in the art will appreciate that to have a controllable or variable current output, it may be desirable to replace constant resistor 128 with a variable resistor. In addition, while current limiting circuit 84 is shown as a resistor, any suitable current limiting circuit configuration may be used. For example, a circuit comprising transistors, resistors, diodes, and the like may be used instead of a simple resistor.

As discussed above, current level monitor/indicator 86 is configured to measure the current output from current limiting circuit 84. In the illustrated embodiment, current level monitor/indicator 86 preferably comprises a device which is configured to measure the voltage across resistor 128, which in turn will give the current flowing through the resistor. However, other current monitoring devices or circuits may be used. In addition, as discussed above with reference to FIG. 2, circuit 55 may further comprise a data acquisition module for collecting therapy and waveform data.

The fundamental difference between the swept and the non-swept waveform is the continuous nature of the spectral characteristics and the time-frequency variation with analog waveforms, and the almost continuous nature (i.e., somewhat discrete) for the spectral characteristics of a swept digital or pulsed waveform. There appears to be some evidence that the human body behaves like a dispersive filter and a waveform that is swept in the appropriate manner may be preferred for electro-therapy. Also, since the physiology and body chemistry for each patient varies, the swept waveform is more likely to provide the optimal frequency which maximizes the therapeutic value for large numbers of people afflicted with various types of visual system diseases.

Figure 5A:
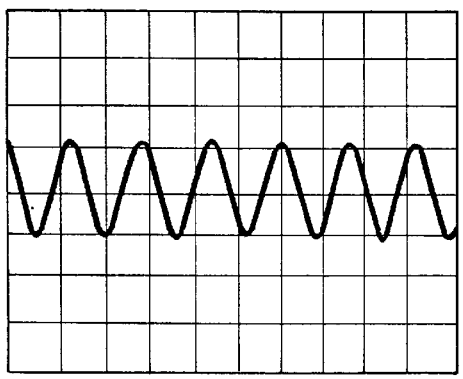
FIG. 5a illustrates a periodic sinusoidal wave signal having a set frequency which is a waveform signal generated by a prior art microcurrent generator.
Figure 5B:
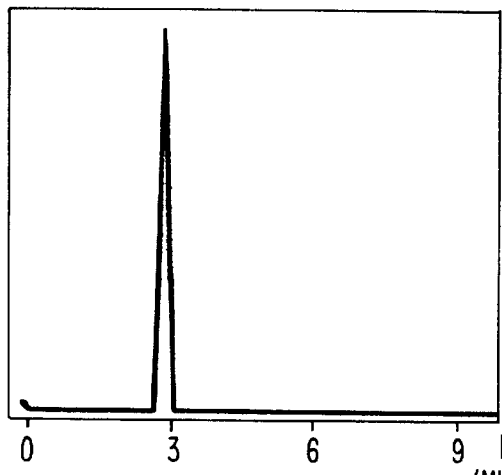

Referring now to FIGS. 5a, 5b, 6a, 6b, 7a, 7b, 8a, and 8b, fundamental differences between discreet frequency wave signals and sweep wave signals is illustrated. Specifically, FIG. 5a illustrates a 2 volt (peak-to-peak) sinusoidal waveform having a set frequency of about 3 MHz. This type of waveform is a typical analog waveform generated by microcurrent stimulation devices currently known in the art. As illustrated in FIG. 5b, the spectral or frequency components of the sinusoidal waveform appear at only one discreet frequency. With this type of signal, all of the power from the signal is located at or near the 3 MHz frequency.

Figure 6A:
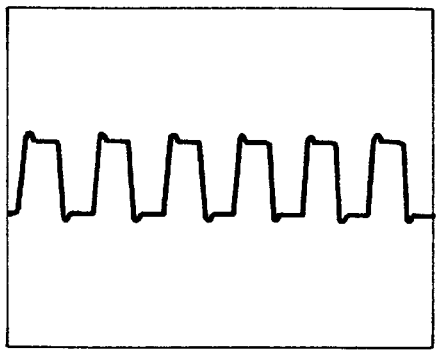
FIG. 6a illustrates a periodic square wave having a set frequency which is a waveform signal generated by a prior art microcurrent generator.
Figure 6B:
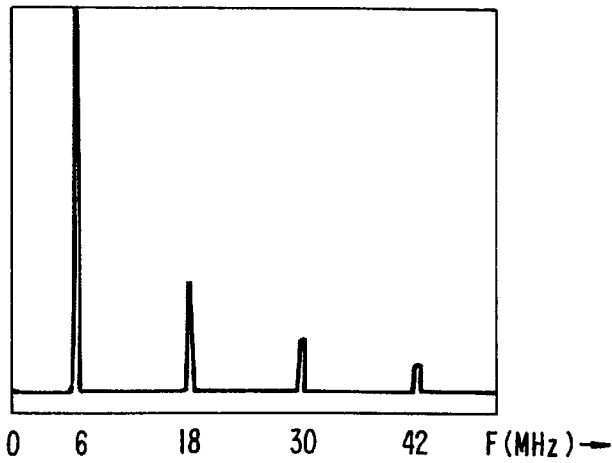

FIG. 6a illustrates a 3.2 volt (peak-to-peak) rectangular waveform having a peak overshoot and a frequency of about 6 MHz. Again, this waveform type is a typical digital or pulsed waveform produced by microcurrent stimulation devices currently known in the art. As illustrated in FIG. 6b, the rectangular waveform has a fundamental frequency component at 6 MHz and diminishing harmonics at 18, 30 and 42 MHz, respectively. With this type of signal, approximately 80% of the power is associated with the fundamental frequency of 6 MHz.

Figure 7A:
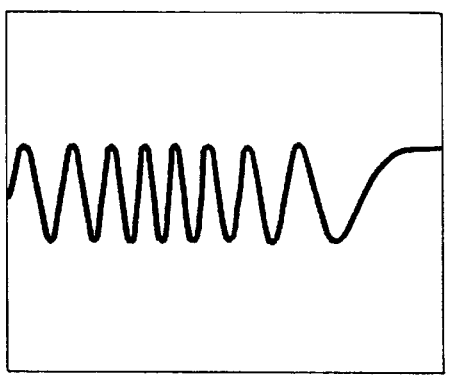
FIG. 7a is a swept sinusoidal waveform signal varying from about 0 Hz to about 125 Hz over a time frame in excess of 100 microseconds.
Figure 7B:
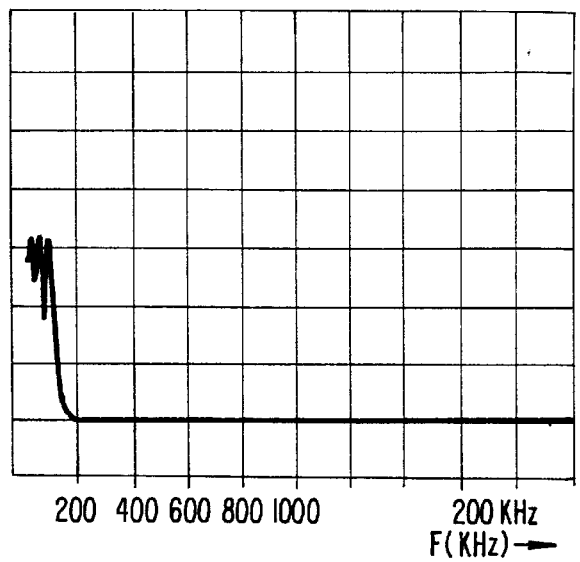

Referring now to FIG. 7a, a 10 volt (peak-to-peak) swept sinusoidal waveform varying from about 0 Hz to about 125 Hz over a time frame of more than 100 microseconds is shown. As illustrated in FIG. 7a, the frequency of the waveform changes with time. FIG. 7b shows the frequency or spectral characteristics of the waveform of FIG. 7a. Specifically, as illustrated FIG. 7b, the frequency or spectral characteristics of the swept analog waveform are continuous, not discreet, like they are with the fixed frequency signal of FIGS. 5b. Thus, the power is not concentrated at one or a few frequencies, but is spread over the entire frequency range. The power at any discreet frequency in the spectrum is 0 watts.

Figure 8A:
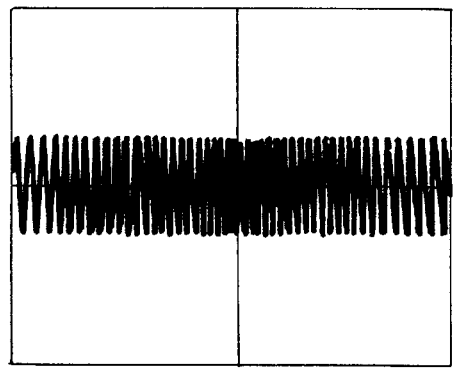
FIG. 8a is a swept sinusoidal waveform varying from about 0 Hz to about 1.1 MHz over a time frame in excess of 1 microseconds.
Figure 8B:
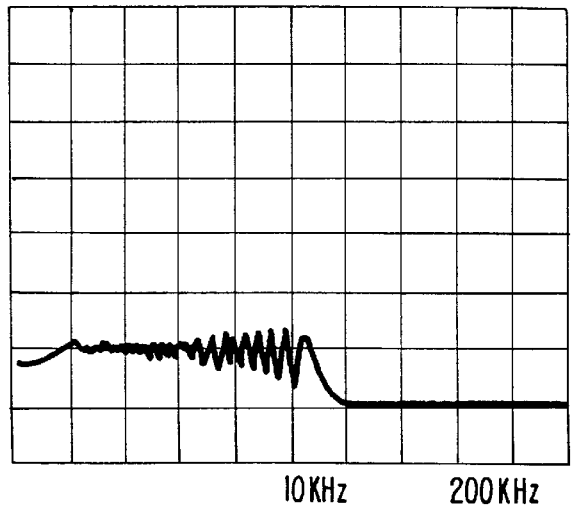

Finally, FIG. 8a illustrates a 10 volt (peak-to-peak) swept sinusoidal waveform varying from 0 Hz to 1.1 MHz over a time frame of more than 100 microseconds is shown. Again, as shown in FIG. 8b, the frequency or spectral characteristics of the swept analog waveform is continuous over the wide frequency range and, thus, the power is spread out over all frequencies. As mentioned briefly above, from the standpoint of patient response variability, such waveform characteristics are preferable for microcurrent stimulation therapy, and in particular, macular degeneration therapy.

Referring now to FIGS. 4a–4d, a method for treating visual system diseases, and in particular, a method for treating macular degeneration will be described. Specifically, to treat macular degeneration, a microcurrent stimulation therapy device, using a swept digital or pulsed signal, similar to the embodiments described above, is used. As mentioned above, in order to create a closed circuit for the microcurrent stimulation device, a brass cylinder or rod preferably is held in one hand of the patient, and a brass microcurrent stimulation probe with a shielded handle is applied to the patient by the therapist. The brass cylinder or rod conducts the electric current allowing the current to pass through the particular body part for therapy.

Figure 4A:
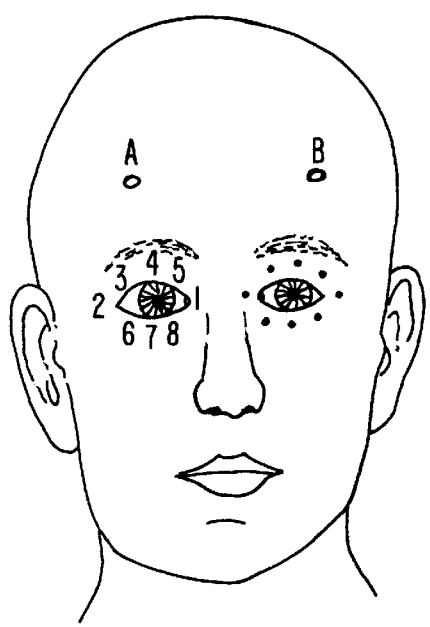
FIG. 4a illustrates eight therapy points around an eyelid to which microcurrent stimulation therapy may be applied in accordance with a method for treating visual system diseases.

In accordance with one embodiment of the present invention, each eye that shows signs of macular degeneration is treated by providing a microcurrent through four points on the upper and four points on the lower eyelid for a total of eight points around the eye. FIG. 4a illustrates the eight points around the eye which are stimulated and the preferred order of stimulation. For example, the stimulation preferably occurs in the order from point one to point eight. When stimulating the eyelid, the patient preferably looks away from the probe with eyes closed. This rolls the macula closer to the stimulation point, keeping the microcurrent from passing through dense eye structures, such as lens, iris and ciliany body, resulting in better microcurrent penetration into the macula region. The eight points around the eye are stimulated using a current between about 50 to about 350 microamps, and more preferably between about 150 and 250 microamps. In accordance with one preferred embodiment of the present invention, the current applied to the eyelid is brought up until the patient sees light flashes and/or feels the tinge of electricity. The current is then decreased so that the patient feels no discomfort. This is the preferred current level used for the therapy.

In accordance with a preferred embodiment of the present invention, each point around the eye is stimulated for about 8 to about 60 seconds, and more preferably for about 30 seconds, using a sweep wave signal. As discussed above, the sweep wave signal may comprise one swept signal, or two independent sweep wave signals combined by an adder/buffer circuit. In accordance with this aspect of the present invention, one of the sweep wave signals preferably comprises a rectangular sweep wave signal having a peak-to-peak voltage of between about 10 to about 30 volts, and more preferably about 20 volts. In addition, the square or rectangular sweep wave signal preferably has a sweep wave frequency range of about 0 to about 400 Hz, and more preferably of about 0 to about 35 Hz; has a sweep time of between about 7 and about 60 seconds, and more preferably of about 15 seconds; and has a duty cycle of between about 20 and about 95 percent, and more preferably of about 75 percent. The other signal generator preferably provides a sweep wave signal having a lower peak-to-peak voltage than the first sweep wave signal. For example, the second sweep wave signal preferably has a peak-to-peak voltage of between about 0.1 to about 4 volts and more preferably about 1 volt, if needed. In addition, the second sweep wave signal preferably has a sweep wave frequency range of about 500 to about 2 MHz, and more preferably of about 500 to about 1.5 MHz; and a sweep time of between about 7 and about 60 seconds, and more preferably of about 15 seconds. The second sweep wave signal may comprise a sinusoidal waveform, a square waveform, a triangular waveform, a ramp waveform, a step waveform, or the like.

In accordance with another preferred embodiment of the present invention, the second signal comprises a non-swept or fixed frequency signal, rather than a swept or sweep wave signal. In accordance with this aspect of the invention, the non-swept wave signal may comprise a sinusoidal wave, a square or rectangular wave, a ramp wave, a step wave, or the like. Preferably, the non-swept wave signal has a peak or peak-to-peak voltage of between about 0.1 to about 4 volts, and more preferably about 1 volt. In addition, the fixed frequency of the non-swept wave signal preferably is in the range of about 500 Hz to 2 MHz, and more preferably in the range of about 500 Hz to 1.5 MHz.

In addition to stimulating points around the eye, the method for treating macular degeneration may include treating other acupuncture or pressure points on the body. For example, as shown in FIG. 4a, there are 2 points, A and B, on the forehead which can be used for microcurrent stimulation. In accordance with this aspect of the present invention, two probes preferably are attached to the frontal area of the forehead at points A and B, and a microcurrent scan is applied to these points for about 10 to 20 minutes, and more preferably for about 15 minutes. In this manner, a relaxation mode of the therapy procedure is applied to the patient. That is, by attaching the electrodes to the forehead of the patient and applying a microcurrent to that location, the conductance of electricity in the head area is increased, thus helping relax the patient, as well as providing other therapeutic affects. For example, in this relaxation mode, some of the microcurrent is scattered toward the eye region, thus supplying additional microcurrent therapy to the eyes.

Figure 4B:
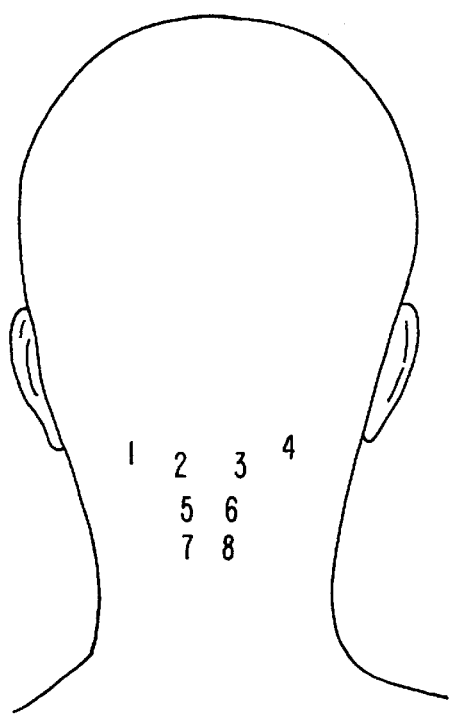
FIG. 4b illustrates eight therapy points on the back of the neck to which microcurrent stimulation therapy may be applied in accordance with a method for treating visual system diseases.
Figure 4C:
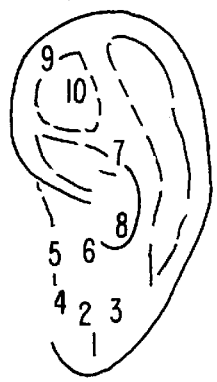
FIG. 4c illustrates ten therapy points on the ear to which microcurrent stimulation therapy may be applied in accordance with a method for treating visual system diseases.
Figure 4D:
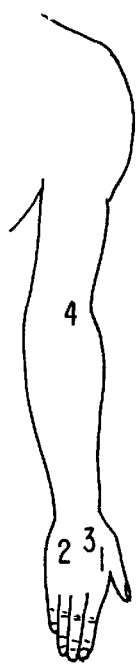
FIG. 4d illustrates four therapy points on an arm to which microcurrent stimulation therapy may be applied in accordance with a method for treating visual system diseases.

In addition, as illustrated in FIG. 4b, there are eight acupuncture or pressure points on the back of the neck which may be stimulated during macular degeneration therapy. In accordance with this aspect of the invention, each pressure point 1–8 is stimulated in ascending order for about 20 to about 60 seconds. Similarly, FIG. 4c shows 10 acupuncture or pressure points on the ear which also may be stimulated for macular degeneration therapy. As with the points around the eye and on the back of the neck, each point 1–10 on the ear is stimulated in ascending order for about 10 to about 30 seconds. Finally, FIG. 4d illustrates four pressure points on an arm which also may be stimulated in the same manner as with the eyes, neck and ears. In accordance with a preferred embodiment of the present invention, similar waveforms are used on the eyes, neck, ears and arms. However, in accordance with other preferred embodiments of the invention, different waveforms may be used on the different body parts, depending on the therapeutic effect of a particular waveform at a particular location.

In accordance with a preferred method for treating macular degeneration, patients initially are treated twice a day for 4 days and 3 times a week thereafter.

Figure 9:
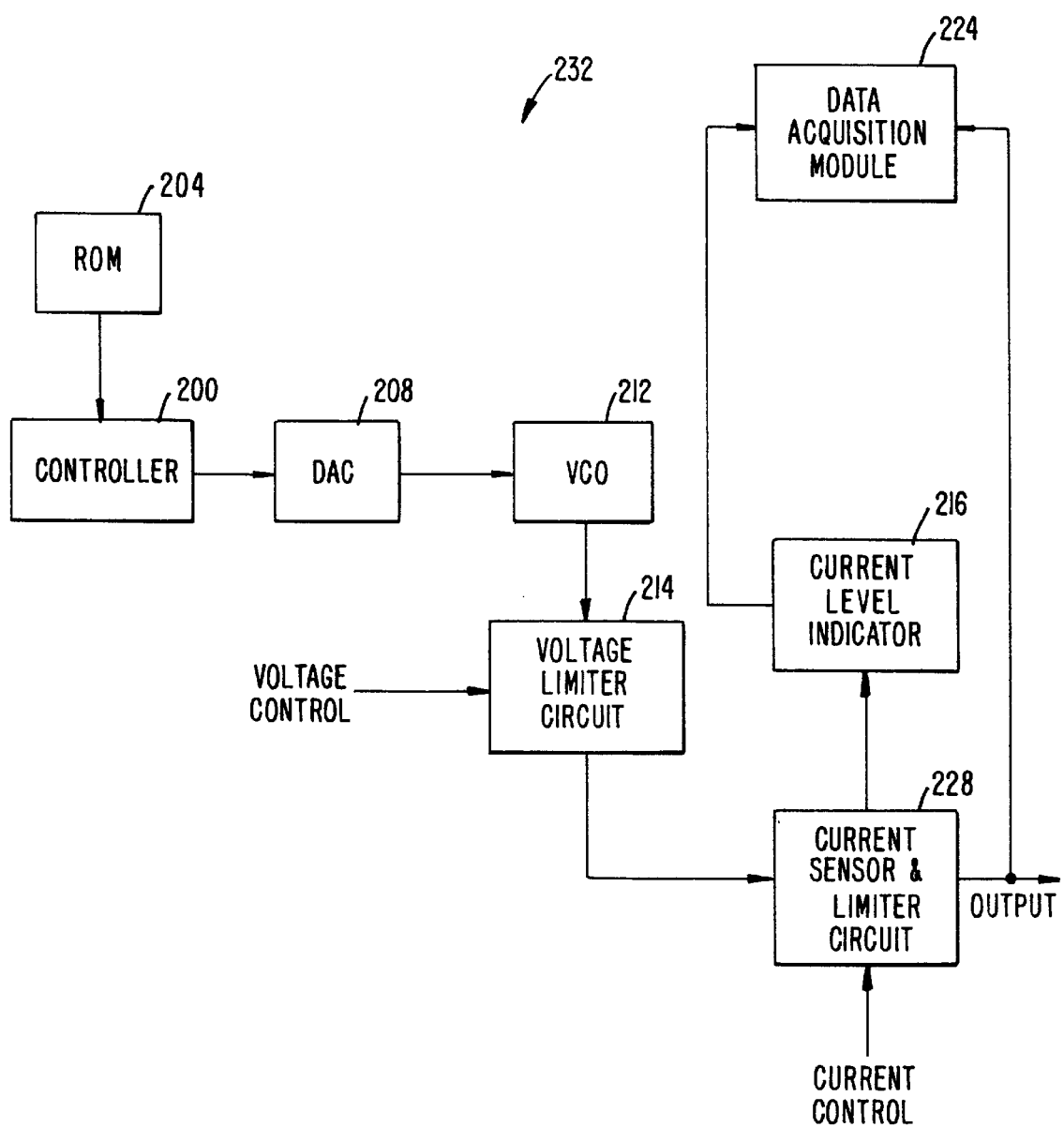
FIG. 9 is an embodiment which allows digital control of the modulation frequency.

With reference to FIG. 9, an embodiment which digitally controls the modulation frequency is shown in block diagram form. This embodiment includes a controller 200, a read only memory (ROM) 204, a digital-to-analog converter (DAC) 208, a voltage controlled oscillator (VCO) 212, a voltage limiter circuit 214, a current level indicator 216, a data acquisition module 224, and a current sensor and limiter circuit 228. These components allow digital frequency modulation (FM) of the output signal produced by the microcurrent stimulation therapy apparatus 232. In other embodiments, an analog waveform generator could also be used in place of parts 200, 204 and 208.

The controller 200 reads values from a lookup table in the ROM 204 to produce a digital word for the DAC 208. The DAC 208 converts a digital word into an analog voltage which is then coupled to the VCO 212. The analog voltage frequency modulates the oscillation of the VCO 212 to produce a modulated frequency. To modify the level of the signal under control from the user, the modulated output from the VCO 212 passes through the voltage limiter circuit 214. The voltage control may be provided by a potentiometer, or other known method.

Monitoring and regulating of the current applied to the patient is performed with a current sensor and limiter circuit 228. The current sensor and limiter circuit 228 regulates the signal to a level selected by the user by using a potentiometer, or the like which is coupled to the current control input. Additionally, the current sensor and limiter circuit 228 passes the signal through a resister so that the current can be sensed as it varies the voltage drop across the resister. To allow application to a patient, the output from the current sensor and limiter circuit 228 is coupled to a probe tip. In this way, the controller can digitally modulate a signal frequency applied to the patient.

The current level indicator 216 displays the current level sensed from the signal and feeds this information to the data acquisition module 224. The indicator 216 can have both visual and audio outputs. For example, it may be a series of LEDs which light up in succession according to the current level. Furthermore, the current level indicator 216 can utilize digital and analog techniques to show the patient the present current applied.

The current measured by the current level indicator 216 is passed to the data acquisition module 224. Additionally, the data acquisition module 224 can record the applied voltage over time so that both current and voltage is known. The physician can download the information from the data acquisition module 224 to analyze the output signal applied to the patient. In other embodiments, the current information could be fed back to the controller such that closed loop feedback could more precisely adjust the output current.

The lookup table within the ROM 204 can store any number of frequency sequences. Additionally, the controller can repeat the entries of the lookup table in a loop to conserve room. Each digital word read from the ROM 204 corresponds to an analog voltage. The analog voltage is applied to the VCO 212 to produce a predetermined modulation frequency. The ROM 204 is preferably a non-volatile and reprogrammable memory device such as an EPROM, an EEPROM, a FLASH memory, or the like. Depending upon the treatment regiment specified, the lookup table within the ROM can be modified by the patient's physician. In this way, any number of frequency sequences can be produced by the therapy apparatus 232.

The digital modulation of the microcurrent stimulation therapy apparatus 232 can provide precision in controlling the spectral response of the signal applied to the patient. Over time, the spectral response exhibits specific frequency components which corresponded to the various frequencies produced by the VCO 212. As described above, the frequency produced by the VCO 212 is achieved from a digital data word stored in a lookup table in the ROM 204. In a non-linear manner, the frequency components from the lookup table could be distributed over the spectrum. The lookup table could sweep the frequency through the spectrum or achieve any different frequency at any time. Therapies for different types of medical conditions my require a more complex spectral response than merely sweeping the frequency from one end of the spectrum to the other. The digital frequency modulation technique could, for example, sweep from 2 KHz through 4 KHz and then sweep from 7 KHz to 9 KHz. To conserve space in the ROM 204, the controller 200 could repeat the delivery of digital data words in a loop to continually repeat the frequency modulation sequence. The wide variety of possible spectral responses allows the therapy apparatus 232 to provide a response that is useful in the treatment of many different health problems such as diseases of the visual system (including macular degeneration and retinitis pigmentosa), orthopedic problems (including sciatica), pain and fatigue disorders (including myofascial pain syndrome, fibromyalgia, sciatica, and neuralgia), and perhaps certain types of cancer (including retinoblastoma cells).

The microcurrent stimulation therapy apparatus 232 can achieve small electronically controlled frequency variations where the change in frequency over time is automatic. This provides the capability to treat a patient with a wider range of frequencies and frequency combinations. As mention above, the waveforms could be unipolar, bipolar or bi-phasic. Unipolar waveforms are characterized by being always positive or always negative; bipolar waveforms are characterized by being both positive and negative, but not necessarily symmetric about the zero potential axis; and bi-phasic waveforms are characterized by being symmetric about the zero potential axis.

This embodiment utilizes frequency modulation (FM), to provide a frequency swept output waveform which distributes the specific frequency components over time. Other embodiments with analog swept sinusoidal output signals which distribute the frequency over time produce a continuous spectral density function. However, in the case of swept digital or pulse waveforms, the spectral density function will also exhibit specific frequency components distributed over time. Accordingly, the spectral density function may also exhibit discrete properties. Digital frequency sweep techniques include (but are not limited to) voltage/current control of an oscillator, programmable frequency division of a oscillating signal and table look-up of the frequency. For example, a programmable number of flip flops could divide a source frequency into any number of lower frequencies. Unlike prior art electro therapeutic systems that require manual frequency changes or small electronically controlled frequency variations, the change in frequency of this embodiment over time is automatic, providing the capability to treat the patient with a wider range of frequencies and frequency combinations.

Figure 10:
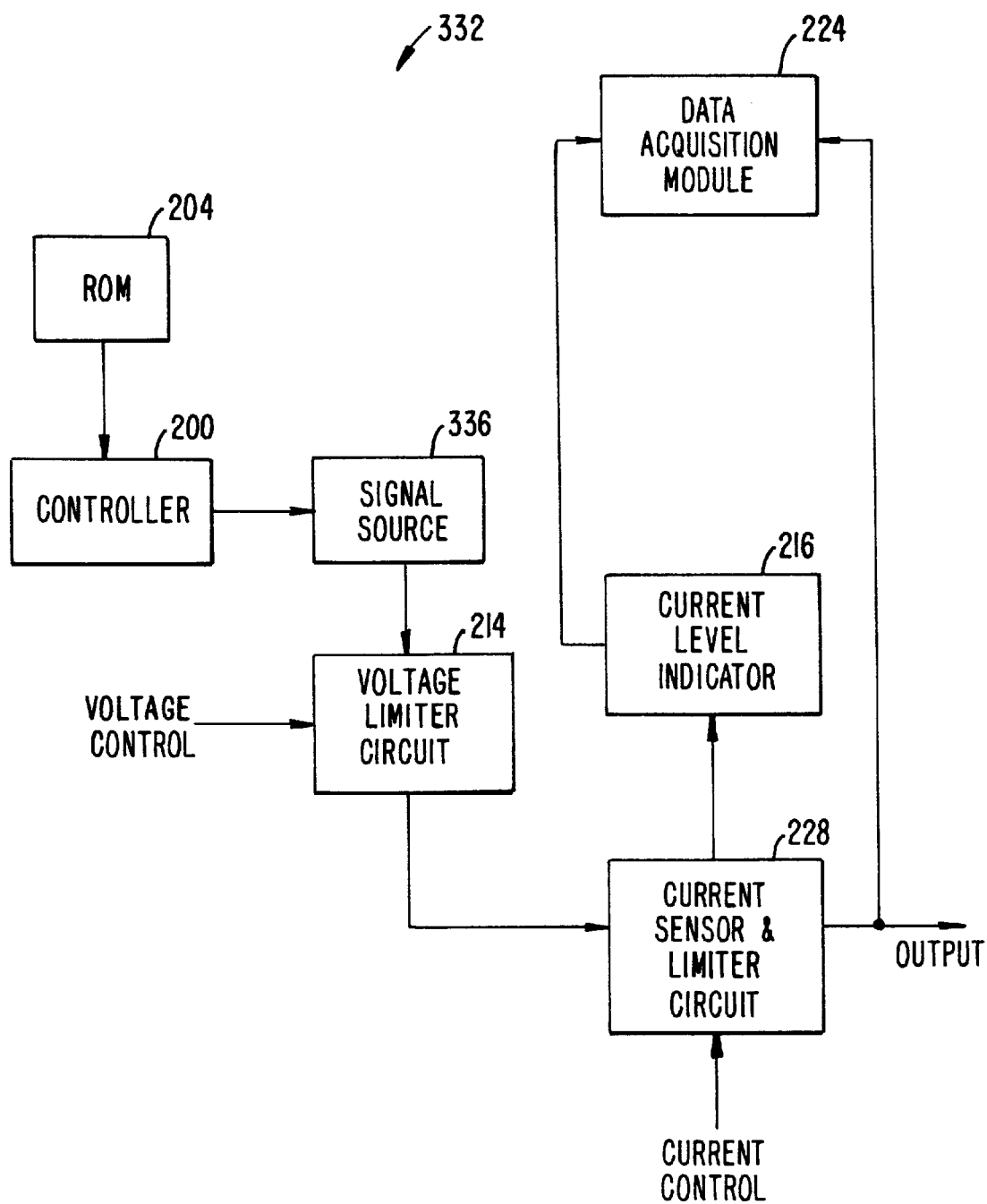
FIG. 10 is an embodiment which produces the output waveform using direct digital synthesis.

With reference to FIG. 10, a microcurrent stimulation therapy apparatus 332, which directly synthesizes the output waveform without using the above described digital modulation technique, is shown in block diagram form. Direct synthesis is the process by which a waveform is recreated by a controller 200 using values from a ROM 204 to control a signal source 336. In the embodiment depicted in FIG. 9, a VCO would not be required and the signal source 208 feeds directly to the current sensor and limiter 228. In this embodiment, the ROM 204 contains a look-up table providing an output to the controller 200 that controls the voltage level of the output signal from the signal source 208. The digital words are reformatted, if necessary, and coupled to the signal source 336. The signal source 208 creates a voltage which corresponds to the digital word.

In essence, the signal source 208 functions as a digital to analog converter in this embodiment. The waveform output from the signal source 208 is comprised of constituent voltage levels which over time create a signal of a single frequency or multiple frequencies. Each constituent voltage corresponds to a digital word from the ROM 204. By using this direct digital synthesis technique, the signal could have any number of predetermined shapes. As can be appreciated by those skilled in the art, use direct digital synthesis allows producing complex waveforms with many constituent frequency components.

To conserve storage space in the ROM 204, only the waveform for a single period need be stored. The controller 200, being aware of the periodic nature of the waveform, could feed the period of the waveform in a continuous loop to recreate the periodic nature of the waveform. A simple example of this is a period which is comprised of a data word of all zeros and a data word of all ones. When fed to the DAC 208 in a loop, the data words would create an oscillating square wave with a period of twice the sampling period of the signal source 336. In this way, waveforms of any shape can be directly digitally synthesized.

Other variations of the circuit in FIG. 10 are also possible. In another embodiment, the controller 200 reads a value from the ROM 204 to produce a voltage. The voltage is coupled to the signal source 336 where the voltage is used to select a oscillation frequency. As the voltage varies, so does the oscillation frequency, such that a range of frequencies is possible as proscribed by the ROM 204. In this embodiment, the signal source 336 performs as a voltage controlled oscillator where the voltage which corresponds to the digital word selects the output frequency. However, it is noted a current could also be used to control the signal source 336.

In yet another embodiment, the controller 200 reads a value from the ROM 204 which corresponds to a pulse. The pulse is created by the controller 200 and fed to the signal source 336. The signal source uses the pulse to select a frequency to generate. By varying the pulse, any number of frequencies are selected.

Figure 11:
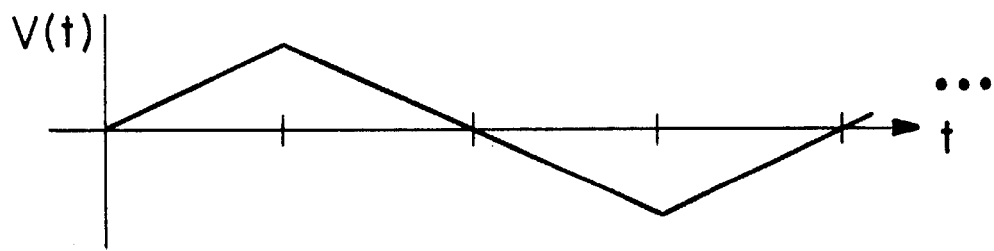
FIG. 11 is an embodiment of a triangular waveform.
Figure 12:
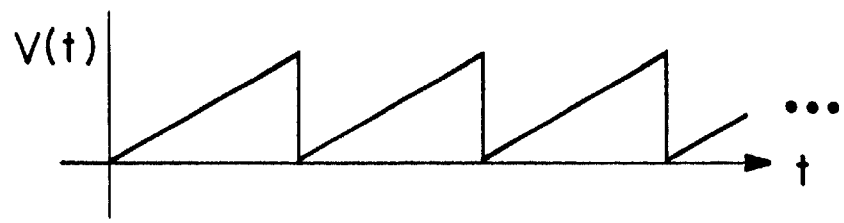
FIG. 12 is an embodiment of a ramp waveform.

With reference to FIGS. 11 and 12, embodiments of a triangular waveform and a ramp waveform are respectively shown. Voltage is shown in the ordinate direction and time is shown along the abscissa.

Figure 13A:
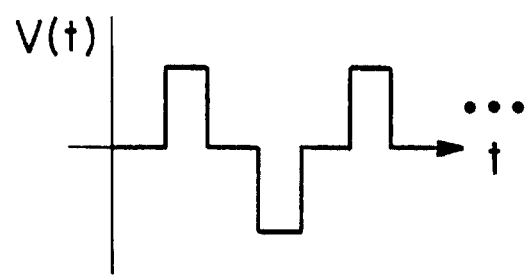
FIG. 13A is a first embodiment of bi-phasic pulses.
Figure 13B:
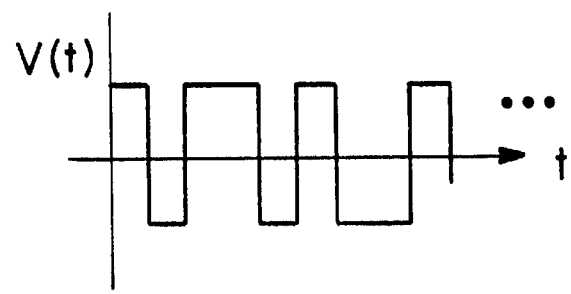
FIG. 13B is a second embodiment of bi-phasic pulses.

Referring next to FIGS. 13A and 13B, embodiments of bi-phasic pulses are shown. More specifically, FIG. 13A shows a bipolar return-to-zero pulse waveform, and FIG. 13B shows a Manchester code pulse waveform. Voltage is shown in the ordinate direction and time is shown along the abscissa. Bi-phasic pulse waveforms have pulses that have a positive and negative polarity and are not necessarily symmetrical with respect to positive and negative polarity.

In conclusion, the present invention provides novel methods and apparatus for using microcurrent stimulation therapy to treat various physiological problems, such as pain, wounds and visual eye diseases. While a detailed description of presently preferred embodiments of the invention have been given above, various alternatives, modifications, and equivalents will be apparent to those skilled in the art. For example, while a particular circuit configuration is given for a sweep wave signal generator of the present invention, various other circuit configurations may be used; such as, digital signal processing circuits or digitally generated wave signal circuits. In addition, while one preferred method for treating macular degeneration is disclosed, other suitable methods may be used to treat macular degeneration, other eye diseases or other chronic problems such as pain and persistent sores. Thus, any number of sweep signal generator circuits and therapy methods may be used without varying from the spirit of the invention. Therefore, the above description should not be taken as limiting the scope of the invention which is defined by the appended claims.

What is claimed is:

1. A method for providing microcurrent stimulation therapy to a body part, comprising the steps of:

receiving a first digital data word;

producing a first frequency related to the first digital data word;

applying a first microcurrent signal at the first frequency to the body part;

receiving a second digital data word;

producing a second frequency related to the second digital data word;

applying a second microcurrent signal at the second frequency to the body part proximate an eye, and limiting a current level of the first and second microcurrent signals applied to the body part.

2. The method as recited in claim 1, wherein the stimulation therapy comprises therapy for treating visual system diseases, and the applying steps include applying the microcurrent signal to an eyelid proximate an eye having a visual system disease.

3. The method as recited in claim 1, wherein the therapy treats at least one of macular degeneration, retinitis pigmentosa, sciatica, pain disorders, fatigue disorders, myofascial pain syndrome, fibromyalgia, neuralgia, and cancer.

4. The method as recited in claim 1, wherein the first microcurrent signal comprises a waveform selected from a group of waveforms comprising a sine wave, a square wave, a triangular wave, a ramp wave, a step wave, an unipolar wave, a bipolar wave, and a bi-phasic wave.

5. The method as recited in claim 1, further comprising the step of limiting a voltage level of the first and second microcurrent signals applied to the body part.

6. The method as recited in claim 1, wherein a current level is in the range of about 50 microamps to about 200 microamps.

7. A method for providing microcurrent stimulation therapy to a body part, comprising the steps of:

receiving a first digital data word;

producing a first analog voltage related to the first digital data word;

applying the first analog voltage to the body part;

inducing a first microcurrent to flow with the first analog voltage;

receiving a second digital data word;

producing a second analog voltage related to the second digital data word;

applying the second analog voltage to the body part proximate an eye having an affliction, wherein the first analog voltage is different from the second analog voltage; and inducing a second microcurrent to flow with the second analog voltage.

8. The method as recited in claim 7, wherein the therapy treats at least one of macular degeneration, retinitis pigmentosa, sciatica, pain disorders, fatigue disorders, myofascial pain syndrome, fibromyalgia, neuralgia, and cancer.

9. The method as recited in claim 7, further comprising the step of producing a periodic waveform which includes the first and second analog voltages, wherein the periodic waveform is selected from the group of waveforms comprising sine wave, square wave, triangular wave, ramp wave, step wave, unipolar wave, bipolar wave, and bi-phasic wave.

10. The method as recited in claim 7, further comprising the step of limiting a current level of the first and second analog voltages applied to the body part.

11. The method as recited in claim 7, further including the step of repeating the forgoing steps a plurality of times to produce a periodic waveform.

12. An apparatus for supplying an electrical signal to a body part in order to provide microcurrent stimulation therapy to the body part, comprising:

a digital-to-analog converter;

a controller coupled to the digital-to-analog converter;

a current limiter coupled to the electrical signal; and a plurality of digital data words, wherein the controller couples the digital data words to the digital-to-analog converter in order to generate the electrical signal.

13. The apparatus as recited in claim 12, further comprising a voltage controlled oscillator, wherein:

the digital-to-analog converter produces an analog voltage which is coupled to the voltage controlled oscillator; and the analog voltage relates to an output frequency of the voltage controlled oscillator.

14. The apparatus as recited in claim 12, wherein a look-up table includes the plurality of digital data words.

15. The apparatus as recited in claim 12, wherein the digital data words are stored in a reprogrammable and non-volatile memory.

16. The apparatus as recited in claim 12, wherein the digital-to-analog converter produces a plurality of voltages which form a periodic waveform.

17. The apparatus as recited in claim 12, further comprising a current limiting circuit coupled to the digital-to-analog converter.

18. The apparatus as recited in claim 12, further comprising a current level indicator which conveys the current level of the electrical signal.

19. The apparatus as recited in claim 12, further comprising a current measuring device adapted to measure the current level of the electrical signal.

20. The apparatus as recited in claim 12, further comprising a data acquisition module for collecting current and voltage level information.

21. A method for providing microcurrent stimulation signals capable of providing therapy to a body part, comprising the steps of:

receiving a first digital data word;

producing a first microcurrent signal related to the first data word;

receiving a second digital data word;

producing a second microcurrent signal related to the second data word; and treating at least one of macular degeneration, retinitis pigmentosa, sciatica, fatigue disorders, myofascial pain syndrome, fibromyalgia, neuralgia, and cancer.

22. A method for providing microcurrent stimulation signals capable of providing therapy to a body part, comprising the steps of:

receiving a data word;

producing a microcurrent signal related to the data word; and applying the microcurrent signal to a point proximate to an eye having a visual system disease.

23. A method for providing microcurrent stimulation signals capable of providing therapy to a body part, comprising the steps of:

receiving a data word;

producing a microcurrent signal related to the data word; and treating at least one of macular degeneration, retinitis pigmentosa, sciatica, fatigue disorders, myofascial pain syndrome, fibromyalgia, neuralgia, and cancer.

* * * * *